United States Patent
Weaver

(10) Patent No.: US 11,453,623 B2
(45) Date of Patent: Sep. 27, 2022

(54) PROCESS FOR THE PRODUCTION OF ALKYLAROMATICS

(71) Applicant: INDORAMA VENTURES OXIDES LLC, The Woodlands, TX (US)

(72) Inventor: Daniel R. Weaver, The Woodlands, TX (US)

(73) Assignee: Indorama Ventures Oxides LLC, The Woodlands, TX (US)

( * ) Notice: Subject to any disclaimer, the term of this patent is extended or adjusted under 35 U.S.C. 154(b) by 59 days.

(21) Appl. No.: 16/649,506

(22) PCT Filed: Jul. 23, 2018

(86) PCT No.: PCT/US2018/043212
§ 371 (c)(1),
(2) Date: Mar. 20, 2020

(87) PCT Pub. No.: WO2019/060034
PCT Pub. Date: Mar. 28, 2019

(65) Prior Publication Data
US 2020/0247729 A1    Aug. 6, 2020

Related U.S. Application Data

(60) Provisional application No. 62/561,924, filed on Sep. 22, 2017.

(51) Int. Cl.
  *C07C 2/70* (2006.01)
  *B01J 19/24* (2006.01)
  *C07C 15/107* (2006.01)
(52) U.S. Cl.
  CPC ............. *C07C 2/70* (2013.01); *B01J 19/2435* (2013.01); *B01J 2219/00051* (2013.01); *C07C 15/107* (2013.01)

(58) Field of Classification Search
None
See application file for complete search history.

(56) References Cited

U.S. PATENT DOCUMENTS

| | | | | | |
|---|---|---|---|---|---|
| 2,988,580 | A | * | 6/1961 | Smith | ........................ C07C 9/16 585/715 |
| 3,014,081 | A | * | 12/1961 | Aldridge | ................... C07C 2/68 585/456 |

(Continued)

FOREIGN PATENT DOCUMENTS

| WO | 2004/072000 | 8/2004 |
|---|---|---|
| WO | 2007/073439 | 6/2007 |

OTHER PUBLICATIONS

International Search Report issued by the United States Patent and Trademark Office dated Oct. 1, 2018, 2 pages.

(Continued)

*Primary Examiner* — Philip Y Louie

(57) ABSTRACT

The present disclosure describes a process for the production of alkylaromatics that may be performed using a loop reactor comprising the steps of: introducing an alkylatable aromatic compound; introducing an olefin; introducing a catalyst; adjusting the alkylatable aromatic compound to a pre-reaction temperature that is below a desired reaction temperature; optionally, adjusting the olefin to a second pre-reaction temperature that is below the desired reaction temperature; optionally, adjusting the catalyst to a third pre-reaction temperature that is below the desired reaction temperature; initially contacting the catalyst and olefin under conditions to control the temperature of the reaction of the catalyst and olefin; mixing and/or circulating the alkylatable aromatic compound, the olefin and the catalyst; and maintaining the alkylatable aromatic compound and olefin at the desired reaction temperature.

17 Claims, 1 Drawing Sheet

(56) References Cited

U.S. PATENT DOCUMENTS

| | | | | |
|---|---|---|---|---|
| 3,437,705 | A | * | 4/1969 | Jones .................... C07C 15/073 585/450 |
| 3,489,818 | A | * | 1/1970 | Hervert .................... C07C 2/62 585/450 |
| 3,755,492 | A | * | 8/1973 | Anderson ................ C07C 2/62 585/703 |
| 4,826,801 | A | | 5/1989 | Bakas et al. |
| 5,157,185 | A | | 10/1992 | Chu et al. |
| 5,434,325 | A | | 7/1995 | Chen et al. |
| 5,770,782 | A | | 6/1998 | Knifton et al. |
| 6,111,159 | A | * | 8/2000 | Huff .......................... C07C 2/18 585/466 |
| 6,486,374 | B1 | | 11/2002 | Radcliffe et al. |
| 2004/0260133 | A1 | | 12/2004 | Guillon et al. |
| 2008/0171900 | A1 | * | 7/2008 | Schmidt .................. B01J 29/70 585/449 |
| 2009/0171133 | A1 | | 7/2009 | Luo et al. |
| 2010/0160703 | A1 | | 6/2010 | Driver et al. |
| 2016/0001255 | A1 | * | 1/2016 | Luo ........................... B01J 14/00 585/728 |

OTHER PUBLICATIONS

Written Opinion of the International Searching Authority issued by the United States Patent and Trademark Office dated Oct. 1, 2018, 5 pages.

Ladnal et al., "Continuous, Ionic Liquid-Catalysed Propylation of Toluene in a Liquid-Liquid Biphasic Reaction Mode using a Loop Reactor Concept", Advanced Synthesis & Catalysis, Mar. 20, 2007, vol. 349, p. 719-726, p. 719, abstract, p. 720, right col, para 3, p. 722, left col, para 3, p. 723, Figure 4, p. 726, left col, para 2.

Buss Chemtech AG, "Advanced BUSS Loop® Reactor Technology", Buss Chemtech Process Technologies, KRESTA Industries, © 2009 Buss ChemTech AG, www.buss-ct.com, Brochure, Oct. 3, 2009, 7 pages.

\* cited by examiner

Replacement Sheet
1/1
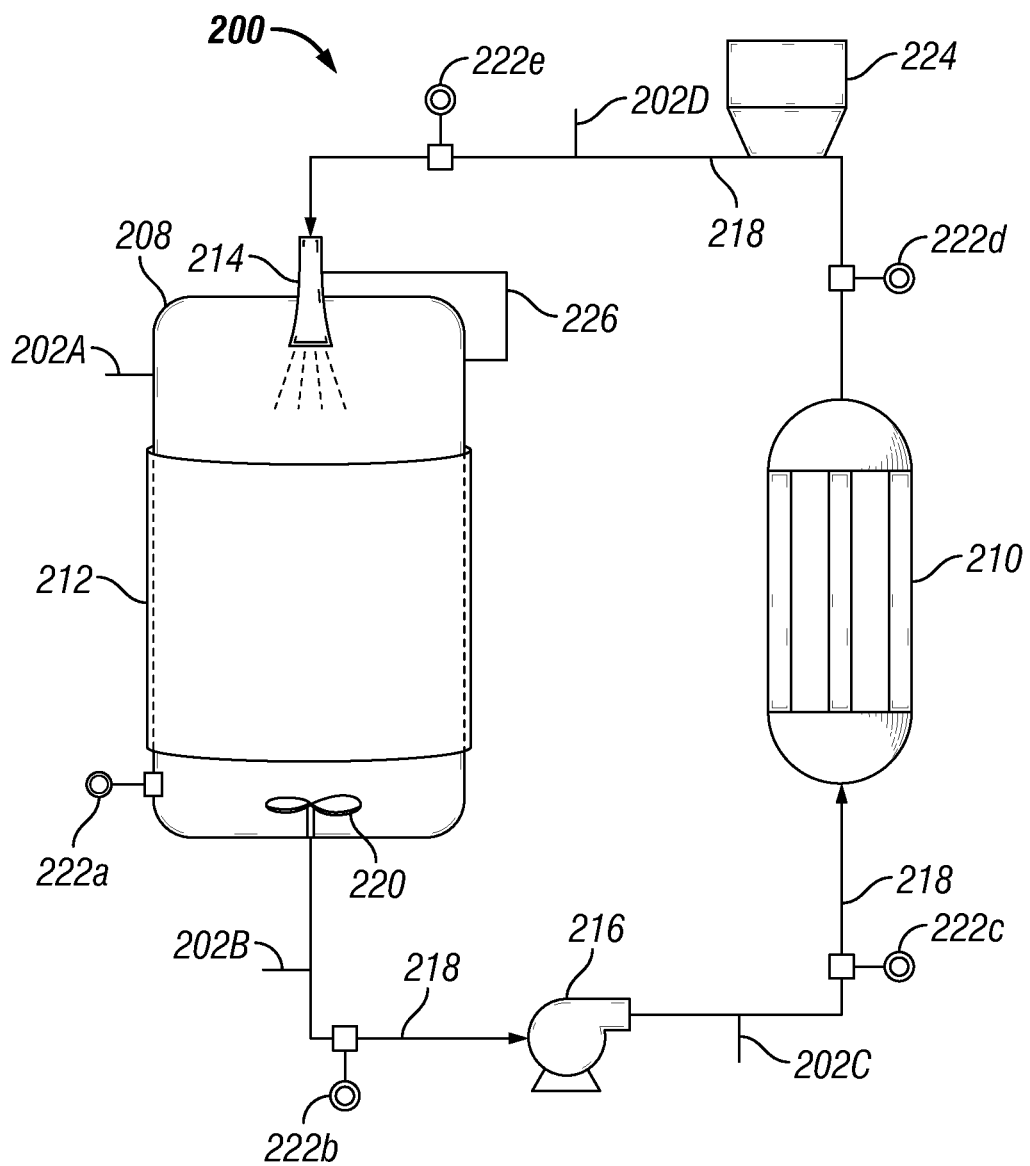
FIGURE

PROCESS FOR THE PRODUCTION OF ALKYLAROMATICS

CROSS REFERENCE TO RELATED APPLICATIONS

The present application claims priority to U.S. Provisional Patent Application Ser. No. 62/561,924, filed on Sep. 22, 2017, the entire contents of which are hereby expressly incorporated herein by reference.

STATEMENT REGARDING FEDERALLY SPONSORED RESEARCH OR DEVELOPMENT

Not applicable.

FIELD OF THE INVENTION

This disclosure relates generally to an alkylation process and, in particular, to an alkylation process that uses temperature-controlled conditions to produce alkylaromatics.

BACKGROUND

Alkylaromatics, such as alkylbenzene, are commonly used as intermediates that are derivatized into detergents that may be used in home and industrial cleaning products. Typically, alkylaromatics are generated by the reaction of alkylatable aromatic compounds and olefins using Friedel-Crafts reaction conditions in a batch or continuous process. These standard processes generally do not offer good temperature control and uniformity of mixing, and as such, the alkylaromatic products produced therefrom generally have broad isomer distributions and varied yields. Having a broader isomer distribution is believed to negatively affect the performance of the detergent. Moreover, the processes that are commonly used involve considerable capital cost based upon the size and amount of equipment necessary to achieve a desired isomer distribution or yield.

SUMMARY

Therefore, it would be desirable to have an improved alkylation process that provides alkylaromatic compounds with tighter isomer distribution and higher yields without considerable capital expenditure costs in equipment.

In an embodiment, an alkylation process is disclosed that includes introducing an alkylatable aromatic compound, an olefin and a catalyst. The process further includes adjusting the alkylatable aromatic compound to a pre-reaction temperature that is below a desired reaction temperature and optionally adjusting the olefin to a second pre-reaction temperature that is below the desired reaction temperature. Optionally, the process may adjust the catalyst to a third pre-reaction temperature that is below the desired reaction temperature. The process initially contacts the catalyst and olefin under conditions to control the temperature of the reaction of the catalyst and olefin; mixes the alkylatable aromatic compound, the olefin and the catalyst; and maintains the alkylatable aromatic compound and olefin at the desired reaction temperature.

According to some embodiments of the present disclosure, the catalyst may be an acid catalyst.

According to some embodiments of the present disclosure, the acid catalyst may be hydrofluoric acid, triflic acid, aluminum chloride, boron trifluoride and combinations thereof.

According to some embodiments of the present disclosure, the alkylatable aromatic compound may be benzene, xylenes, toluene, cumene, ethylbenzene, butylbenzene, naphthalene, alkyl naphthalenes and combinations thereof.

According to some embodiments of the present disclosure, the alkylatable aromatic compound is a substituted aromatic compound comprising the formula:

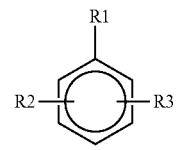

wherein R1 is a hydrogen or an alkyl group containing from about 1 to 4 carbon atoms; R2 is hydrogen or an alkyl group having from about 1 to 4 carbon atoms; and R3 is an alkyl group having from about 14 to about 60 carbon atoms.

According to some embodiments of the present disclosure, the olefin is at least one $C_8$ or higher olefin.

According to some embodiments of the present disclosure, the olefin is at least one $C_{14}$ to $C_{60}$ olefin.

According to some embodiments of the present disclosure, the alkylation process introduces a diluent and optionally, adjusts the diluent to a fourth pre-reaction temperature that is below a desired reaction temperature.

According to some embodiments of the present disclosure, initially contacting the catalyst and olefin under conditions to control the temperature of the reaction of the catalyst and olefin includes contacting the catalyst and olefin at a point before the catalyst and olefin pass through a heat exchanger.

According to some embodiments of the present disclosure, initially contacting the catalyst and olefin under conditions to control the temperature of the reaction of the catalyst and olefin includes contacting the catalyst and olefin incrementally over a period of 1 minute to 120 minutes.

According to some embodiments of the present disclosure, the pre-reaction temperature, second pre-reaction temperature and third pre-reaction temperature are each temperatures about 2 to about 60 degrees Celsius below the desired reaction temperature.

In another embodiment, an alkylation process is disclosed that includes providing a loop reactor comprising a reaction chamber and a heat exchanger. The reaction chamber and the heat exchanger are in fluid communication with each other via at least one conduit such that a fluid in the reaction chamber can be circulated through the heat exchanger and returned to the reaction chamber. The process further introduces an alkylatable aromatic compound, an olefin and a catalyst into the loop reactor. The process further adjusts the alkylatable aromatic compound to a pre-reaction temperature that is below a desired reaction temperature and optionally adjusts the olefin to a second pre-reaction temperature that is below the desired reaction temperature. The process may optionally adjusts the catalyst to a third pre-reaction temperature that is below the desired reaction temperature. The process initially contacts the catalyst and olefin in the conduit circulating fluid from the reaction chamber to the heat exchanger. The process circulates the alkylatable aromatic compound, the olefin and the catalyst in the loop reactor and maintains the alkylatable aromatic compound and olefin at the desired reaction temperature.

According to some embodiments of the present disclosure, an alkylation process may further include mixing the alkylatable aromatic compound, the olefin and the catalyst in the loop reactor.

According to some embodiments of the present disclosure, the loop reactor may include a pump.

According to some embodiments of the present disclosure, an akylation process adjusts the alkylatable aromatic compound to a pre-reaction temperature by circulating the alkylatable aromatic compound through the heat exchanger.

According to some embodiments of the present disclosure, an alkylation process adjusts the olefin to a second pre-reaction temperature that is below the desired reaction temperature by circulating the olefin through the heat exchanger.

According to some embodiments of the present disclosure, an alkylation process adjusts the olefin to a second pre-reaction temperature before initially contacting the catalyst and olefin in the conduit circulating fluid from the reaction chamber to the heat exchanger.

According to some embodiments of the present disclosure, an alkylation process introduces the catalyst into the loop reactor by adding the catalyst in the conduit circulating fluid from the reaction chamber to the heat exchanger.

According to some embodiments of the present disclosure, an alkylation process introduces an olefin into the loop reactor by adding the olefin in the conduit circulating fluid from the reaction chamber to the heat exchanger.

According to some embodiments of the present disclosure, an alkylation process further introduces a diluent into the loop reactor and optionally, adjusts the diluent to a fourth pre-reaction temperature that is below a desired reaction temperature.

BRIEF DESCRIPTION OF THE DRAWING

The present disclosure may be better understood, and its numerous features and advantages made apparent to those skilled in the art by referencing the accompanying drawing.

The included Figure is a schematic illustration of an exemplary loop reactor that may be used in alkylation processes of the present disclosure.

DETAILED DESCRIPTION

If appearing herein, the term "comprising" and derivatives thereof are not intended to exclude the presence of any additional component, step or procedure, whether or not the same is disclosed herein. In order to avoid any doubt, all compositions claimed herein through use of the term "comprising" may include any additional additive or compound, unless stated to the contrary. In contrast, the term, "consisting essentially of" if appearing herein, excludes from the scope of any succeeding recitation any other component, step or procedure, except those that are not essential to operability and the term "consisting of", if used, excludes any component, step or procedure not specifically delineated or listed. The term "or", unless stated otherwise, refers to the listed members individually as well as in any combination.

The articles "a" and "an" are used herein to refer to one or to more than one (i.e. to at least one) of the grammatical objects of the article. By way of example, "an olefin" means one olefin or more than one olefin.

The phrases "in one embodiment", "according to one embodiment", "in embodiments of the present disclosure", "according to some embodiments", and the like generally mean the particular feature, structure, or characteristic following the phrase is included in at least one embodiment of the present disclosure, and may be included in more than one embodiment of the present disclosure. Importantly, such phrases do not necessarily refer to the same embodiment. If the specification states a component or feature "may", "can", "could", or "might" be included or have a characteristic, that particular component or feature is not required to be included or have the characteristic.

As discussed above, it is desirable to have alkylaromatics with a tight isomer distribution and less isomer variability. For example, when producing alkylbenzene, it is typically beneficial to achieve a desirable amount of 2-phenyl isomers in the product. These goals may be achieved when the alkylation process for producing alkylaromatics provides for good temperature control and uniform mixing. In particular, it is desirable to have uniform temperature and composition throughout the reactor.

According to one embodiment, an alkylation process for producing alkylaromatics is provided that involves the steps of introducing an alkylatable aromatic compound, introducing an olefin; introducing a catalyst, adjusting the alkylatable aromatic compound to a pre-reaction temperature that is below a desired reaction temperature, optionally, adjusting the olefin to a second pre-reaction temperature that is below the desired reaction temperature, optionally, adjusting the catalyst to a third pre-reaction temperature that is below the desired reaction temperature, initially contacting the catalyst and olefin under conditions to control the temperature of the reaction of the catalyst and olefin, mixing or circulating the alkylatable aromatic compound, the olefin and the catalyst, and maintaining the alkylatable aromatic compound and olefin at the desired reaction temperature.

According to an embodiment, an alkylation process involves the step of introducing an alkylatable aromatic compound. Generally, the alkylatable aromatic compound may be any aromatic compound that is able to undergo an alkylation reaction. Any one or more useful aromatic compounds and/or any useful alkyl benzene or mixture thereof may serve as an alkylatable aromatic compound. The term "aromatic" in "alkylatable aromatic compound" is to be understood in accordance with its art-recognized scope. This includes alkyl substituted and unsubstituted mono- and poly-cyclic compounds.

Examples of alkylatable aromatic compounds include, without limitation, benzene, toluene, xylenes, cumene, ethylbenzene, butylbenzene, naphthalene, alkyl-naphthalenes and combinations thereof. Other examples of alkylatable aromatic compounds include, without limitation, anthracene, naphthacene, perylene, coronene, phenanthrene and combinations thereof, including combinations with the other alkylatable aromatic compounds listed in this disclosure.

Alkylatable aromatic compounds may include substituted aromatic compounds. Substituted aromatic compounds that can be alkylated herein must possess at least one hydrogen atom directly bonded to the aromatic ring. The aromatic rings can be substituted with one or more alkyl, aryl, alkaryl, alkoxy, aryloxy, cycloalkyl, halide, and/or other groups that do not interfere with the alkylation reaction. Generally the alkyl groups that can be present as substituents on the aromatic compound contain from 1 to about 22 carbon atoms and usually from about 1 to 8 carbon atoms, and most usually from about 1 to 4 carbon atoms. A substituted aromatic compound may have the general formula:

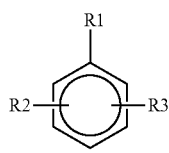

wherein R1 is a hydrogen or an alkyl group containing from about 1 to 4 carbon atoms; R2 is hydrogen or an alkyl group having from about 1 to 4 carbon atoms; and R3 is an alkyl group having from about 14 to about 60 carbon atoms.

Suitable alkyl substituted aromatic compounds include isopropylbenzene, n-propylbenzene, alpha-methylnaphthalene, mesitylene, durene, cymenes, pseudocumene, o-diethylbenzene, m-diethylbenzene, p-diethylbenzene, isoamylbenzene, isohexylbenzene, pentaethylbenzene, pentamethylbenzene; 1,2,3,4-tetraethylbenzene; 1,2,3,5-tetramethylbenzene; 1,2,4-triethylbenzene; 1,2,3-trimethylbenzene, m-butyltoluene; p-butyltoluene; 3,5-diethyltoluene; o-ethyltoluene; p-ethyltoluene; m-propyltoluene; 4-ethyl-m-xylene; dimethylnaphthalenes; ethylnaphthalene; 2,3-dimethylanthracene; 9-ethylanthracene; 2-methylanthracene; o-methylanthracene; 9,10-dimethylphenanthrene; 3-methyl-phenanthrene; hexylbenzene, nonylbenzene, dodecylbenzene, pentadecylbenzene, hexyltoluene, nonyltoluene, dodecyltoluene, pentadecytoluene and combinations thereof. Alkyl substituted aromatic compounds would also include toluene, xylene, ethylbenze and butylbenzene as listed above.

Different alkylatable aromatic compounds and/or combinations of alkylatable aromatic compounds would be used depending on their costs, structures and the desired end products.

Other alkylatable compounds that may be used in the present disclosure include reformate, which is a product of hydrocarbon reforming. Reformate contains a mixture of benzene, toluene and/or xylene.

Embodiments of the present disclosure include introducing one or more olefins. Olefins that may be useful generally include any hydrocarbons having one or more available unsaturated bonds capable of reaction with the alkylatable aromatic compound. Olefins, also called alkenes or olefines, are unsaturated hydrocarbons. By unsaturated it means that there is at least one pair of carbon atoms linked by a double bond or triple bond. Acyclic olefins with a single double bond have the general formula $C_nH_{2n}$.

In embodiments of the present disclosure, the olefin used may be any $C_5$ or higher olefin. $C_2$ to $C_4$ olefins are typically gaseous at ordinary temperatures and pressures. Rather, $C_5$ or higher olefins are typically liquid at ordinary temperatures and pressures. These olefins may be straight chained or branched. In embodiments of the present disclosure, the olefin used may be any $C_6$ or higher olefin. In embodiments of the present disclosure, the olefin used may be any $C_7$ or higher olefin. In embodiments of the present disclosure, the olefin used may be any $C_8$ or higher olefin. In embodiments of the present disclosure, the olefin used may be any $C_9$ or higher olefin. In embodiments of the present disclosure, the olefin used may be any $C_{10}$ or higher olefin. In embodiments of the present disclosure, the olefin used may be any $C_{11}$ or higher olefin. In embodiments of the present disclosure, the olefin used may be any $C_{12}$ or higher olefin.

In embodiments of the present disclosure, the olefin used may be any higher olefin in the range of $C_{14}$ to $C_{60}$. Olefins in this range are typically oil soluble, which makes them suitable for use in the production of alkylaromatics that might later be incorporated into detergents for oil products.

In embodiments of the present disclosure, the weight ratio of alkylatable aromatic compound to olefin may be in the range of about 0.3 to about 10.

Suitable commercially available olefins may include AlphaPlus® Normal.

Alpha Olefins available from Chevron Phillips Chemical Company and NEODENE* linear alpha and internal olefins available from the Shell Group of companies.

Embodiments of the present disclosure include introducing one or more catalysts. The catalysts may generally include any catalysts capable of encouraging the reaction between the olefin and the alkylatable aromatic compound. In embodiments of the present disclosure, the catalyst may include any suitable acid catalyst that has a pH of less than about 3. Such acid catalysts include, but are not limited to, hydrofluoric acid, triflic acid, aluminum chloride, boron trifluoride and combinations thereof. Such acid catalysts may be liquids or solids.

Fluidized solid catalysts, such as those comprising zeolite and aluminosilicate compounds with sufficient pore openings, may also be used. The use of solid catalysts for this reaction may require additional machinery and equipment for proper delivery of the solids to the process and proper filtration and collection of the spent solid catalysts as can be seen in catalyst hopper 224 in the Figure. The use of a solid catalyst will also influence the desired or target reaction temperature.

Commercially available catalysts may include hydrofluoric acid available from Honeywell International Inc.

The amount of catalyst used may be in the range of about 0.1 to about 20 weight ratio based on the weight of the olefin. In an embodiment, the weight ratio of catalyst to olefin may be in the range of about 0.1 to about 20. The amount of the catalyst may be adjusted according to certain factors such as the desired conversion and dispersability. If the amount of catalyst used is too low, the conversion of the alkylatable aromatic compound to the desired alkylaromatic may decrease and the amount of undesired isomer by-products, such as the presence of 2-phenyl isomers may increase. If the amount of catalyst used is too high, it becomes more difficult to disperse the catalyst into the organic phase resulting in the catalyst being a diluent, which slows down the reaction. In the case of fluidized solid catalysts, the weight ratio of catalyst to olefin should not exceed a ratio of 20 in order provide ideal catalyst contact.

According to an embodiment, an alkylation process involves the optional step of introducing one or more diluents. Generally, the diluents may be any compounds that are unreactive to the alkylatable aromatic compound, the olefin and the catalyst. Having a diluent is useful to slow down the reaction rate and promote the formation of desired isomers. An example of a diluent is, without limitation, paraffin. The diluents used herein may include one or more diluents. One skilled in the art, with the benefit of this disclosure, will recognized other suitable diluents based on the reactants and catalysts used in the reaction.

The term, "introducing" as in "introducing an alkylatable aromatic compound" generally means adding the alkylatable aromatic compound to the reactor. Adding the alkylatable aromatic compound to the reactor may involve adding the alkylatable aromatic compound to the reaction chamber or any part of the reactor. This may also be referred to as "charging" the alkylatable aromatic compound to the reactor. Similarly, the term introducing has the same meaning for the term, "introducing an olefin," "introducing a catalyst,"

and "introducing a diluent," as it does for "introducing an alkylatable aromatic compound." Referring to the Figure, such exemplary introduction points for introducing the alkylatable aromatic compound, olefin, catalyst and diluent into loop reactor 200 are show in lines 202A, 202B, 202C and 202D.

There are a multiple options for the order of the introduction of alkylatable aromatic compounds, olefins, catalysts and diluents to the reactor. In an embodiment, the alkylatable aromatic compound and olefin are first introduced into the reactor. Then the catalyst is introduced into the reactor. The diluent may be introduced with either the alkylatable aromatic compound and the olefin or the catalyst.

In an embodiment, the catalyst may be first introduced into the reactor and then the aromatic compound and olefin are introduced into the reactor. Once again, the diluent may be introduced with either the alkylatable aromatic compound and the olefin or the catalyst.

In an embodiment, the alkylatable aromatic compound and the catalyst are first introduced into the reactor, then the olefin is introduced into the reactor. The diluent may be introduced with either the alkylatable aromatic compound and the catalyst or the olefin.

In an embodiment of the present disclosure, the alkylatable aromatic compound is adjusted to a pre-reaction temperature that is below a desired reaction temperature. This adjusting may occur prior to introduction to the reactor or after introduction to the reactor. This adjusting may involve heating or cooling the alkylatable aromatic compound to the pre-reaction temperature. Prior to introduction to the reactor, the alkylatable aromatic compound may be heated or cooled by means available at the facility. After introduction to the reactor, the adjusting may take place by running the alkylatable aromatic compound through a heat exchanger 210 or by using reactor jacket 212 as shown in the Figure.

Embodiments of the present disclosure include adjusting the alkylatable aromatic compound to a pre-reaction temperature that is below a desired reaction temperature. The pre-reaction temperature will be below the desired reaction temperature if the reaction is exothermic or above the desired reaction temperature if the reaction is endothermic. The amount of difference between the pre-reaction temperature and desired reaction temperature depends on the amount of heat generated or heat lost in the reaction of the reactants. If the reaction is not very exothermic or endothermic, the pre-reaction temperature and desired reaction temperature may be the same. When producing alkylbenzenes, the initial reaction between the catalyst and olefin is exothermic and leads to an initial spike in temperature of the reaction. Having a pre-reaction temperature below the desired reaction temperature helps to stabilize the temperature of the entire reaction and is thought to reduce the number of 2-phenyl isomers in the product.

In embodiments of the present disclosure, the alkylatable aromatic compound is adjusted from about 2 to about 60 degrees Celsius below the desired reaction temperature. In embodiments of the present disclosure, the alkylatable aromatic compound is adjusted to about 2, 4, 6, or 8 degrees Celsius below the desired reaction temperature. In embodiments of the present disclosure, the alkylatable aromatic compound is adjusted to about 10, 12, 14, 16 or 18 degrees Celsius below the desired reaction temperature. In embodiments of the present disclosure, the alkylatable aromatic compound is adjusted to about 20, 22, 24, 26 or 28 degrees Celsius below the desired reaction temperature. In embodiments of the present disclosure, the alkylatable aromatic compound is adjusted to about 30, 32, 34, 36 or 38 degrees Celsius below the desired reaction temperature. In embodiments of the present disclosure, the alkylatable aromatic compound is adjusted to about 40, 42, 44, 46 or 48 degrees Celsius below the desired reaction temperature. In embodiments of the present disclosure, the alkylatable aromatic compound is adjusted to about 50, 52, 54, 56 or 58 degrees Celsius below the desired reaction temperature. In embodiments of the present disclosure, the alkylatable aromatic compound is adjusted to about 60 degrees Celsius below the desired reaction temperature. For the purposes of this disclosure, the ranges between the above values are also included. For example, the above disclosure would disclose the range of the alkylatable aromatic compound being adjusted from about 6 to about 12 degrees Celsius below the desired reaction temperature.

In embodiments of the present disclosure, the alkylatable aromatic compound is adjusted to a pre-reaction temperature that is a point above its freezing point and below the desired reaction temperature. If benzene is the alkylatable aromatic compound, it may be adjusted to above its freezing point of 5.5 degrees Celcius. The temperature adjustment may occur prior to introduction to the reactor or once it is in the reactor, for example, by means of a heat exchanger. This temperature adjustment may be carried out using a heat exchanger or by other means known in the art.

The desired reaction temperature would be the ideal temperature for the reactants to react in order to produce the desired products. It is thought that maintaining a stable desired reaction temperature produces products that are more uniform, having less isomers and undesired by-products. Uniform mixing may help promote more uniform reaction temperatures. In embodiments of the present disclosure, the desired reaction temperature is from about 8 to about 12 degrees Celsius. In embodiments of the present disclosure, the desired reaction temperature is about 10 degrees Celsius. In embodiments of the present disclosure, the desired reaction temperature is from about 20 to about 24 degrees Celsius. In embodiments of the present disclosure, the desired reaction temperature is from about 33 to about 43 degrees Celsius. In embodiments of the present disclosure, the desired reaction temperature is about 38 degrees Celsius. In embodiments of the present disclosure, the desired reaction temperature is from about 50 to about 60 degrees Celsius. In embodiments of the present disclosure, the desired reaction temperature is about 55 degrees Celsius. In embodiments of the present disclosure, the desired reaction temperature is about 22 degrees Celsius. In embodiments of the present disclosure, the desired reaction temperature is from about 60 to about 100 degrees Celsius. In embodiments of the present disclosure, the desired reaction temperature is from about 76 to about 82 degrees Celsius. In embodiments of the present disclosure, the desired reaction temperature is about 77 degrees Celsius. In embodiments of the present disclosure, the desired reaction temperature is from about 95 to about 105 degrees Celsius. In embodiments of the present disclosure, the desired reaction temperature is about 100 degrees Celsius. One skilled in the art, with the benefit of this disclosure, will be able to determine an appropriate desired reaction temperature for a reaction by studying the products made at different temperatures.

In an embodiment, the process includes, optionally, adjusting the olefin to a second pre-reaction temperature that is either above or below the desired reaction temperature. The adjusting may include heating or cooling the olefin to a desired temperature. In embodiments of the present disclosure, the olefin is adjusted to about 2, 4, 6, or 8 degrees Celsius below the desired reaction temperature. In embodiments of the present disclosure, the olefin is adjusted to about 10, 12, 14, 16 or 18 degrees Celsius below the desired reaction temperature. In embodiments of the present disclosure, the olefin is adjusted to about 20, 22, 24, 26 or 28 degrees Celsius below the desired reaction temperature. In embodiments of the present disclosure, the olefin is adjusted to about 30, 32, 34, 36 or 38 degrees Celsius below the desired reaction temperature. In embodiments of the present disclosure, the olefin is adjusted to about 40, 42, 44, 46 or 48 degrees Celsius below the desired reaction temperature. In embodiments of the present disclosure, the olefin is adjusted to about 50, 52, 54, 56 or 58 degrees Celsius below the desired reaction temperature. In embodiments of the present disclosure, the olefin is adjusted to about 60 degrees Celsius below the desired reaction temperature. For the purposes of this disclosure, the ranges between the above values are also included. For example, the above disclosure would disclose the range of the olefin being adjusted from about 24 to about 32 degrees Celsius below the desired reaction temperature.

The temperature adjustment for the olefin may similarly occur prior to introduction to the reactor or once it is in the reactor, for example, by means of a heat exchanger or reactor jacket. The temperature adjustment of the olefin may be done in the same manner as adjusting the alkylatable aromatic compound as described above.

If both the alkylatable aromatic compound and olefin are in the reactor at the same time, prior to introducing the catalyst, the temperatures of the alkylatable aromatic compound and the olefin may be adjusted simultaneously.

In an embodiment, the process includes, optionally, adjusting the catalyst to a third pre-reaction temperature that is either above or below the desired reaction temperature. This may be desirable when the catalyst is a liquid catalyst or a solid catalyst that is suspended in a liquid. The adjusting may include heating or cooling the catalyst to a desired temperature. In embodiments of the present disclosure, the catalyst is adjusted to about 2, 4, 6, or 8 degrees Celsius below the desired reaction temperature. In embodiments of the present disclosure, the catalyst is adjusted to about 10, 12, 14, 16 or 18 degrees Celsius below the desired reaction temperature. In embodiments of the present disclosure, the catalyst is adjusted to about 20, 22, 24, 26 or 28 degrees Celsius below the desired reaction temperature. In embodiments of the present disclosure, the catalyst is adjusted to about 30, 32, 34, 36 or 38 degrees Celsius below the desired reaction temperature. In embodiments of the present disclosure, the catalyst is adjusted to about 40, 42, 44, 46 or 48 degrees Celsius below the desired reaction temperature. In embodiments of the present disclosure, the catalyst is adjusted to about 50, 52, 54, 56 or 58 degrees Celsius below the desired reaction temperature. In embodiments of the present disclosure, the catalyst is adjusted to about 60 degrees Celsius below the desired reaction temperature. For the purposes of this disclosure, the ranges between the above values are also included. For example, the above disclosure would disclose the range of the catalyst being adjusted from about 38 to about 44 degrees Celsius below the desired reaction temperature.

The temperature adjustment for the catalyst may similarly occur prior to introduction to the reactor or once it is in the reactor, for example, by means of a heat exchanger or reactor jacket. The temperature adjustment of the catalyst may be done in the same manner as adjusting the alkylatable aromatic compound as described above.

If both the alkylatable aromatic compound and catalyst are in the reactor at the same time, prior to introducing the olefin, the temperatures of the alkylatable aromatic compound and the catalyst may be adjusted simultaneously.

In an embodiment, the process includes, optionally, adjusting the diluent to a fourth pre-reaction temperature that is either above or below the desired reaction temperature. In embodiments of the present disclosure, the diluent is adjusted to about 2, 4, 6, or 8 degrees Celsius below the desired reaction temperature. In embodiments of the present disclosure, the diluent is adjusted to about 10, 12, 14, 16 or 18 degrees Celsius below the desired reaction temperature. In embodiments of the present disclosure, the diluent is adjusted to about 20, 22, 24, 26 or 28 degrees Celsius below the desired reaction temperature. In embodiments of the present disclosure, the diluent is adjusted to about 30, 32, 34, 36 or 38 degrees Celsius below the desired reaction temperature. In embodiments of the present disclosure, the diluent is adjusted to about 40, 42, 44, 46 or 48 degrees Celsius below the desired reaction temperature. In embodiments of the present disclosure, the diluent is adjusted to about 50, 52, 54, 56 or 58 degrees Celsius below the desired reaction temperature. In embodiments of the present disclosure, the diluent is adjusted to about 60 degrees Celsius below the desired reaction temperature. For the purposes of this disclosure, the ranges between the above values are also included. For example, the above disclosure would disclose the range of the catalyst being adjusted from about 38 to about 44 degrees Celsius below the desired reaction temperature.

The temperature adjustment for the diluent may similarly occur prior to introduction to the reactor or once it is in the reactor, for example, by means of a heat exchanger or reactor jacket. The temperature adjustment of the diluent may be done in the same manner as adjusting the alkylatable aromatic compound as described above.

If the alkylatable aromatic compound, olefin and diluent are in the reactor at the same time, prior to introducing the catalyst, the temperatures of the alkylatable aromatic compound, olefin and diluent may be adjusted simultaneously. Similarly, if the alkylatable aromatic compound, catalyst and diluent are in the reactor at the same time, prior to introducing the olefin, the temperatures of the alkylatable aromatic compound, catalyst and diluent may be adjusted simultaneously.

Embodiments of the present disclosure further include the step of initially contacting the catalyst and olefin under conditions to control the temperature of the reaction of the catalyst and olefin. Because the initial reaction between the catalyst and olefin is exothermic, it is done under conditions to control the temperature of the reaction of the catalyst and olefin. It is thought that controlling this initial spike in reaction temperature reduces isomers distribution typically generated in this reaction. This step may be done by introducing the catalyst or olefin together at a point before they are both passed through heat exchanger 210. For example, if the olefin was already in the loop reactor 200 and the catalyst was then inserted through line 202C or 202B, then the heat of the initial reaction between the catalyst and olefin would be absorbed by heat exchanger 210 and thereby under conditions to control the temperature of the reaction of the catalyst and olefin. The same result can be achieved if the catalyst was already in loop reactor 200 and then the olefin was inserted through line 202C or 202B. Once again, the heat of the initial reaction between the catalyst and olefin would be absorbed by heat exchanger 210 and thereby under conditions to control the temperature of the reaction of the catalyst and olefin. Having the catalyst and olefin initially contacting at the entry points of lines 202A and 202D in loop reactor 200 would be less desirable because they would have a longer time to react before passing through heat exchanger 210. However, if the turnover rate of the loop reactor 200 is high, then catalyst and olefin may be initially contacted at the entry points of lines 202A and 202D without much difference in final alkylaromatic products produced.

Embodiments of the present disclosure may further control the temperature of the reaction of the catalyst and olefin by gradually or slowly contacting the catalyst and olefin. Instead of rapidly adding the entire portion of the catalyst or olefin to the reactor, the catalyst or olefin is incrementally added over a period of time. If the olefin is already in the reactor, this may be done by incrementally adding the catalyst to the reactor over a period of 1 minute to 180 minutes. In some embodiments the catalyst is incrementally added to the reactor over a period of 10 minutes to 60 minutes. If the catalyst is already in the reactor, then the olefin is incrementally added to the reactor over a period of 1 minute to 180 minutes. In some embodiments the olefin is incrementally added to the reactor over a period of 10 minutes to 60 minutes.

In embodiments of the present disclosure, such incremental adding of the catalyst or olefin may be done in a period of 1 minute, 5 minutes, 10 minutes, 15 minutes, 20 minutes, 25 minutes, 30 minutes, 35 minutes 40 minutes, 45 minutes, 50 minutes, 55 minutes, 60 minutes, 65 minutes, 70 minutes, 75 minutes, 80 minutes, 85 minutes, 90 minutes, 95 minutes, 100 minutes, 105 minutes, 110 minutes, 115 minutes, 120 minutes, 130 minutes, 140 minutes, 150 minutes, 160 minutes, 170 minutes or 180 minutes.

Embodiments of the present disclosure further comprise the step of mixing the alkylatable aromatic compound, the olefin, the catalyst and optional diluent. This step allows for the olefin that has been activated by the catalyst to come in contact and react with the alkylatable aromatic compound to produce the akylaromatic product. Mixing may be done by means known in the art. In loop reactor 200, circulating the alkylatable aromatic compound, the olefin and the catalyst through the loop reactor will provide mixing. A loop reactor that has a high turnover or circulation rate of the reactants, preferably a turnover or circulation rate in the range of 0.1 to 20 reactor volumes per minute (based on the type of reaction vessel and reactant amounts), will result in the good mixing.

Additional mixing is thought to occur while the alkylatable aromatic compound, the olefin, the catalyst and the optional diluent pass through pump 216 and heat exchanger 210.

Particular components may be part of loop reactor 200 to increase mixing. For example, nozzle 214, gas recirculation line 226 and mechanical mixer 220 may be part of loop reactor 200 to provide further mixing of the alkylatable aromatic compound, the olefin, the catalyst and the optional diluent. Nozzle 214 is a spray nozzle that further diffuses the mixture, preferably by creating a turbulent flow. Nozzle 214 may further be combined with gas recirculation line 226. Gas recirculation line 226 circulates gas from reaction chamber 208 to conduit 218 or nozzle 214 to further mix the alkylatable aromatic compound, the olefin, the catalyst and the optional diluent. Also, reaction chamber 208 may include mechanical mixer 220. Mechanical mixer 220 may be a mixing mechanism, such as a propeller mixer or agitator, in reaction chamber 208. Mechanical mixer 220 help promotes uniform mixing of the reactants.

Embodiments of the present disclosure include the step of maintaining the alkylatable aromatic compound and olefin at the desired reaction temperature. The continued reactions of the olefin and catalyst and the reaction of the alkylatable aromatic compound and activated olefin are exothermic and will continue to raise the temperature of the reaction mixture. In embodiments of the present disclosure, the reaction temperature is maintained at a desired reaction temperature by such means as using heat exchanger 210. By circulating the reactants, catalyst, diluents and products through heat exchanger 210 the desired reaction temperature is maintained. Reactor jacket 212 may also be used to maintain a desired reaction temperature. It is also believed that the uniform mixing of the alkylatable aromatic compound and olefin helps to maintain the alkylatable aromatic compound and olefin at the desired reaction temperature.

The alkylation processes described herein can be performed at temperatures in the range of −20° C. to 300° C. and pressures in the range of −14.696 psig to 2000 psig. Depending upon the type of catalyst and olefin used and the kind of alkylaromatic product sought, the target or desired reaction temperatures for the reactions may be about 100° C., about 77° C., about 55° C., about 38° C., about 22° C., about 20° C., about 10° C., or those described earlier.

Embodiments of the present disclosure further include an alkylation process that provides a loop reactor with a reaction chamber and a heat exchanger, wherein the reaction chamber and the heat exchanger are in fluid communication with each other via at least one conduit such that a fluid in the reaction chamber can be circulated through the heat exchanger and returned to the reaction chamber. The process introduces, not necessarily at the same time, an alkylatable aromatic compound, an olefin, and a catalyst into the loop reactor. The process adjusts the alkylatable aromatic compound to a pre-reaction temperature that is below a desired reaction temperature and optionally, adjusts the olefin to a second pre-reaction temperature that is below the desired reaction temperature. The process optionally adjusts the catalyst to a third pre-reaction temperature that is below the desired reaction temperature. The catalyst and olefin are initially contacted in the conduit circulating fluid from the reaction chamber to the heat exchanger. The process circulates the alkylatable aromatic compound, the olefin and the catalyst in the loop reactor and maintains the alkylatable aromatic compound and olefin at the desired reaction temperature. In an embodiment of the present disclosure, the process mixes the alkylatable aromatic compound, the olefin and the catalyst in the loop reactor.

An exemplary loop reactor 200 that may be used in alkylation processes of the present disclosure is shown in the Figure. Referring to the Figure, loop reactor 200 comprises reaction chamber 208, heat exchanger 210, reactor jacket 212, conduit 218, lines 202A, 202B, 202C and 202D, pump 216, nozzle 214, temperature sensors 222*a*, 222*b*, 222*c*, 222*d*, 222*e*, gas recirculation line 226, mechanical mixer 220 and solid catalyst hopper 224. Not all of these components are needed, for example, gas recirculation line 226 and mechanical mixer 220 may be added to improve mixing. Also solid catalyst hopper 224 may not be needed if a liquid catalyst is used.

Loop reactor 200 has reaction chamber 208. Although the reactions occur throughout loop reactor 200, this is the primary chamber for the alkylatable aromatic compound, olefin and catalyst to react. Reaction chamber 208 may include line 202A that allows entry of the alkylatable aromatic compound, olefin, catalyst and/or diluent into reaction chamber 208. Line 202A also may function to remove the alkylatable aromatic compound, olefin, catalysts, diluents and/or alkylaromatic products ("reactor contents") out of reaction chamber 208. Reaction chamber 208 may also include additional mixing means such as mechanical mixer 220, nozzle 214 and gas recirculation line 226. Reaction chamber 208 may also include temperature sensor 222a to monitor the pre-reaction temperature of the alkylatable aromatic compound, the second pre-reaction temperature of the olefin, the third pre-reaction temperature of the catalyst and the fourth pre-reaction temperature of the diluent. Temperature sensor 222a may also be used to monitor the reaction temperature.

Loop reactor 200 has heat exchanger 210. Heat exchanger 210 can be any device used to transfer heat. The heat exchanger 210 may be a standard shell-and-tube heat exchanger in which brine water passes through the shell of the heat exchanger 210 for cooling or heating the alkylatable aromatic compound, olefin, catalyst and optional diluent which flow through the tube portion of the heat exchanger 210.

Heat exchanger 210 may be used to add or remove heat from the alkylatable aromatic compound, olefin, catalyst and/or diluent. For example heat exchanger 210 may adjust the alkylatable aromatic compound to a pre-reaction temperature. This may involve heating or cooling the alkylatable aromatic compound. Similarly, heat exchanger 210 may adjust the temperature of the olefin to a second pre-reaction temperature, adjust the catalyst to a third pre-reaction temperature and adjust the diluent to a fourth pre-reaction temperature. When the alkylatable aromatic compound and olefin are in loop reactor 200 with the catalyst and optional diluent, heat exchanger 210 may serve to keep the temperature of the alkylatable aromatic compound, olefin, catalyst and optional diluent at a desired reaction temperature. One skilled in the art will recognize suitable heat exchangers to use for embodiments of the present disclosure.

Reaction chamber 208 and heat exchanger 210 are in fluid communication with one another through conduit 218 such that fluids in reaction chamber 208 can be circulated through heat exchanger 210 and returned to reaction chamber 208. Conduit 218 is a line that serves to transfer fluids and any solid catalyst in the fluids. Conduit 218 serves the purpose of circulating, either individually or together, the alkylatable aromatic compound, the olefin, the catalyst and optional diluent through heat exchanger 210 and delivering it back to reaction chamber 208. In this manner conduit 218 circulates the reactor contents through loop reactor 200.

Loop reactor 200 may additionally have pump 216. Pump 216 serves to provide a means for circulating the reactor contents in loop reactor 200. In doing so, pump 216 helps regulate the temperature of the system by circulating the reactor contents to pass through heat exchanger 210. Pump 216 may also increase mixing by increasing the turnover rate in loop reactor 200.

Along conduit 218 may exist various lines that serve as entry points or exit points for loop reactor 200. The Figure includes lines 202B, 202C and 202D between reaction chamber 208 and heat exchanger 210. These entry points allow a user to add or remove reactor contents from loop reactor 200.

Along conduit 218 may also exist additional temperature sensors 222b, 222c, 222d and 222e. It may desirable to have these temperature sensors after lines 202B, 202C and 202D and after heat exchanger 210 in order to monitor the temperature of the reactor contents.

Reaction chamber 208 may have reactor jacket 212. Reactor jacket 212 serves to adjust or maintain the temperature of the contents with reaction chamber 208. Reactor jacket 212 serves a similar function as heat exchanger 210. Reactor jacket 212 may be an external jacket that surrounds reaction chamber 208. Reactor jacket 212 may have tubes and/or coils filled with heat transfer fluid. The heat transfer fluid passes through the jacket to add or remove heat from reaction chamber 208.

In an embodiment of the present disclosure, a solid catalyst may be used. If a solid catalyst is used, loop reactor 200 may include solid catalyst hopper 224. Solid catalyst hopper 224 may include a means for adding solid catalyst to a loop reactor 200 and may also include means for removing solid catalyst from loop reactor 200.

Loop reactor 200 may adjust the alkylatable aromatic compound to a pre-reaction temperature that is below a desired reaction temperature by circulating the alkylatable aromatic compound through conduit 218 to heat exchanger 210. Similarly, loop reactor 200 may adjust the olefin to a second pre-reaction temperature that is below the desired reaction temperature by circulating the olefin through conduit 218 to heat exchanger 210. Loop reactor 200 may also adjust the catalyst to a third pre-reaction temperature that is below a desired reaction temperature by circulating the catalyst through conduit 218 to heat exchanger 210. Finally, loop reactor 200 may adjust the diluent to a fourth pre-reaction temperature that is below the desired reaction temperature by circulating the olefin through conduit 218 to heat exchanger 210.

The temperature of the alkylatable aromatic compound, olefin, catalyst and optional diluent introduced to loop reactor 200 may be monitored using one or more temperature sensors 222a, 222b, 222c, 222d and 222e.

In an embodiment of the present disclosure, adjusting the temperatures of the alkylatable aromatic compound, olefin, catalyst and optional diluent may be conducted outside of the loop reactor 200 before these components are introduced to the loop reactor 200. The alkylatable aromatic compound, the olefin, catalyst and optional diluent may be introduced to the loop reactor 200 at a variety of different entry points at lines 202A, 202B, 202C and 202D.

In embodiments of the present disclosure, loop reactor 200 may adjust the alkylatable aromatic compound to a pre-reaction temperature that is below a desired reaction temperature by introducing the alkylatable aromatic compound into reaction chamber 208 through line 202A. The alkylatable aromatic compound remains in reaction chamber 208 as reactor jacket 212 is used to adjust the alkylatable aromatic compound to a pre-reaction temperature. Temperature sensor 222a may be used to monitor the temperature. Similarly, loop reactor 200 may adjust the olefin to a second pre-reaction temperature that is below the desired reaction temperature by introducing the olefin through line 202A into reaction chamber 208 and having reactor jacket 212 adjust the temperature. Loop reactor 200 may also adjust the catalyst to a third pre-reaction temperature that is below a desired reaction temperature by introducing the catalyst through line 202A into reaction chamber 208 and having reactor jacket 212 adjust the temperature. Finally, loop reactor 200 may adjust the diluent to a fourth pre-reaction temperature that is below a desired reaction temperature by introducing the catalyst through line 202A into reaction chamber 208 and having reactor jacket 212 adjust the temperature.

Embodiments of the present disclosure initially contact the catalyst and olefin in the conduit circulating fluid from the reaction chamber to the heat exchanger. In an embodiment, the catalyst is introduced into loop reactor 200 by adding the catalyst at line 202B and/or 202C into conduit 218 that is circulating fluid from the reaction chamber to the heat exchanger. This would be preferable when the alkylatable aromatic compound and the olefin have already been added to loop reactor 200. This enables the heat exchanger 210 to help buffer a heat spike that results from the olefin coming into contact with the catalyst. In other embodiments of the present disclosure, the catalyst is introduced in to loop reactor 200 by adding the catalyst at line 202D.

In an embodiment, the catalyst and olefin are initially contacted in the conduit circulating fluid from the reaction chamber to the heat exchanger by introducing the olefin into loop reactor 200 by adding the olefin at line 202B and/or 202C into conduit 218 that is circulating fluid from the reaction chamber to the heat exchanger. This would be preferable when the alkylatable aromatic compound and the catalyst have already been added to loop reactor 200. In other embodiments of the present disclosure, the olefin is introduced in to loop reactor 200 by adding the olefin at line 202D.

Embodiments of the process include the step of circulating the alkylatable aromatic compound, the olefin, the catalyst and the optional diluent in loop reactor 200. The circulation may be carried out, in one aspect, by circulating the reactor contents through conduit 218 (using pump 216) from reaction chamber 208 to the heat exchanger 210 and delivered back to reaction chamber 208. The circulation of the reactor contents may be performed at a high circulation or turnover rate within loop reactor 200, which also contributes to mixing of the alkylatable aromatic compound, the olefin, the catalyst and the optional diluent in loop reactor 200. In some embodiments, a turnover or circulation rate may be in the range of 0.1 to 20 loop reactor volumes per minute.

In embodiments of the present disclosure, the process further includes mixing the alkylatable aromatic compound, the olefin, the catalyst and the optional diluent in loop reactor 200. Mixing of the reactor contents may be done with nozzle 214 (such as a spray nozzle) that provides turbulent flow of the reactor contents. In addition to nozzle 214, a gas recirculation line 226 may be added to loop reactor 200. Gas recirculation line 226 may be connected between reaction chamber 208 and nozzle 214 or conduit 218. Gas recirculation line 226 adds vapors and gases into the liquid before exiting nozzle 214. Nozzle 214 and gas recirculation line 226 may be designed so as to create gas flow mixing in reactor 208 by bubbling. This bubbling action helps promote uniform mixing and temperatures in loop reactor 200.

In embodiments of the present disclosure, a mechanical mixer 220, such as an agitator, may be added to reaction chamber 208 as another tool to aid the mixing of the reactor contents.

In embodiments of the present disclosure, the process further includes the step of maintaining the alkylatable aromatic compound and olefin at the desired reaction temperature. This step may be accomplished by circulating the alkylatable aromatic compound and olefin through loop reactor 200 that has heat exchanger 210 to regulate the temperature of the alkylatable aromatic compound and olefin and using one or more temperature sensors 222$a$, 222$b$, 222$c$, 222$d$ and/or 222$e$ (or another temperature sensor) to monitor the temperature of the reaction so that a desired reaction temperature can be maintained. In an embodiment of the present disclosure, reaction chamber 208 has reactor jacket 212 that may also be used to regulate the temperature of the alkylatable aromatic compound, olefin and catalyst at a desired reaction temperature. One skilled in the art will recognize other appropriate methods to maintain the reaction at a desired reaction temperature.

The loop reactors of the present disclosure may be set up to operate in a batch mode or a continuous mode. The Figure exemplifies a possible batch mode. However, this process can also be conducted in a continuous mode. The continuous mode may include multiple loop reactors in series or parallel.

Embodiments of the present disclosure include an alkylation process that occurs in a single pot batch reactor. The single pot batch reactor process would have a reaction chamber with a means for regulating the temperature of the reaction chamber, such as reactor jacket 212. The reaction chamber may also have an mechanical mixer 220 to increase mixing.

Once the reaction is completed, the alkylaromatic product may be drawn off or delivered to a separation vessel for isolation and further analyzed to determine the conversion of the olefin and the isomer distribution. Lines 202A, 202B, 202C and 202D may be used to remove the alkylaromatic product and remaining alkylatable aromatic compound, olefin, catalyst and optional diluent.

In embodiments of the present disclosure, the alkylation processes may have increased olefin conversion, the alkylaromatic product may have a tighter isomer distribution, the reaction time of the alkylation process may be reduced, and the reactor effluent may contain fewer less valuable co-products.

In embodiments of the present disclosure, the alkylaromatic product does not contain more than 16% of the 2-phenyl isomer. In embodiments of the present disclosure, the alkylaromatic product does not contain more than 15% of the 2-phenyl isomer. In embodiments of the present disclosure, the alkylaromatic product does not contain more than 14% of the 2-phenyl isomer. In embodiments of the present disclosure, the alkylaromatic product does not contain more than 13% of the 2-phenyl isomer. In embodiments of the present disclosure, the alkylaromatic product does not contain more than 12% of the 2-phenyl isomer. In embodiments of the present disclosure, the alkylaromatic product does not contain more than 11% of the 2-phenyl isomer. In embodiments of the present disclosure, the alkylaromatic product does not contain more than 10% of the 2-phenyl isomer.

The advantages of the alkylation processes disclosed are further illustrated by the following examples. However, the following non-limiting examples are not intended to be all-inclusive and are not intended to limit the scope of the embodiments described herein.

Example 1

Four runs of the following reaction were completed in a loop reactor similar to the loop reactor represented in the Figure: olefin+benzene→alkylbenzene in the presence of triflic acid catalyst.

The desired reaction temperature target was 10 degrees Celsius (° C.), measured using the temperature sensor located on the reaction chamber (similar location as temperature sensor 222$a$). 4.895 kilograms (kg) of olefin and 6.364 kg of benzene were charged to the loop reactor and mixed, by circulation, with cooling on the heat exchanger to a temperature of 8° C. Next, 2.741 kg of triflic acid catalyst was added to the loop reactor at a point between the reaction chamber and pump (line 202B). The catalyst addition time was 152 minutes for Run 1, 38 minutes for Run 2, 37 minutes for Run 3 and 27 minutes for Run 4. The catalyst, olefin and benzene were circulated in the loop reactor to complete the reaction. Run 1 was circulated for 40 minutes. Run 2 was circulated for 30 minutes, Run 3 was circulated for 61 minutes. Run 4 was circulated for 77 minutes. During the reaction, the temperature was maintained between 8° C. and 12.4° C. with target of 10° C. After completion of the reaction, the product was transferred to a separation vessel and the organic phase was separated. The organic phase was treated with 0.5 kg of calcium oxide (CaO) and mixed for an hour. The excess benzene was removed and the remaining product was then analyzed. The results of the analysis of the products are reflected in Table 1.

TABLE 1

| Example 1 | Run 1 | Run 2 | Run 3 | Run 4 |
|---|---|---|---|---|
| Lights, % | 6.7 | 6.5 | 6.4 | 6.4 |
| SPGR 60/60 | 0.862 | 0.864 | 0.862 | 0.861 |
| Iodine #, g/100 g | 0.9 | 0.9 | 1.1 | 1.0 |
| Yield, % | 91.7 | 92.0 | 92.3 | 92.3 |

The measurements reflected in Table 1 are those that are critical to the performance of the alkylbenzene as an intermediate that can be further derived for use as a lubricant or detergent. The Lights are the lighter alkylbenzenes formed in the reaction. These lights are lower in value and represent a yield loss. The specific gravity (SPGR) is a measure of the molecular weight of the isomer distribution. The Iodine # is a measure of conversion of the olefin. Finally, the Yield refers the yield of the reaction.

The results in Table 1 show good results for the four runs. The Lights show a low percentage of unwanted lighter alkylbenzenes (6.4-6.7%) formed in the reaction. It is not atypical for the Lights to vary from 10 to 45% in current comparative commercial alkylation processes. The SPGR values for Runs 1-4 indicate very good control over the isomer distribution with little variance between the runs. It is not atypical for the SPGR to vary over 0.005 between runs in current comparative commercial alkylation processes. The Iodine # values also vary little in Runs 1-4. It is not atypical to have Iodine #s to vary over 0.75 to 1.5 in current comparative commercial alkylation processes. The Yield for the alkylation processes conducted in Runs 1-4, which are about 92% or greater for each run, are very good. It is not atypical to have yields that are lower, around 55% to 90% in current comparative commercial alkylation processes.

Example 2: Isomer Distribution

Six runs of the following reaction were completed in a 50-liter loop reactor similar to the loop reactor represented in the Figure: olefin+benzene→alkylbenzene in the presence of triflic acid catalyst.

The desired reaction temperature target was 20° C., measured using the temperature sensor located on the reaction chamber (similar location as temperature sensor 222a). 16.4 kg of olefin and 21.3 kg of benzene were charged to the loop reactor and mixed, by circulation, with cooling on the heat exchanger to a temperature of about 8° C. Next, 9.2 kg of triflic acid catalyst was added to the loop reactor at a point between the reaction chamber and pump (line 202B). The catalyst was incrementally added to the loop reactor during a 5 minute time period. The catalyst, olefin and benzene were circulated in the loop reactor for 40 minutes to complete the reaction. During the reaction, the temperature was maintained between 18° C. and 22° C. with target of 20° C. After completion of the reaction, the product was transferred to a separation vessel and the organic phase was separated. The organic phase was treated with 2.3 kg of CaO and mixed for an hour. The excess benzene was removed and the remaining product was then analyzed. The results of the analysis of the products are reflected in Table 2.

TABLE 2

| Example 2 | Lights, % |
|---|---|
| Run 5 | 6.8 |
| Run 6 | 7.1 |
| Run 7 | 6.8 |
| Run 8 | 7.0 |
| Run 9 | 6.1 |
| Run 10 | 7.2 |

The results in Table 2 shows the percentage of unwanted lighter alkylbenzenes were measured between 6.1 to 7.2%. These runs show a consistent and tight isomer distribution of desirable alkylbenzene reaction products.

Example 3: 2-Phenyl Isomer

Four runs of the following reaction were completed in a batch reactor: olefin+paraffin+benzene→alkylbenzene in the presence of hydroflouric acid catalyst.

First, 70.4 grams (g) of hydrofluoric acid catalyst was charged to the reaction chamber. Next, 66.8 g of benzene and 66.8 g of paraffin were charged to the reaction chamber. The hydrofluoric acid catalyst, benzene and paraffin (diluent) were stirred mechanically and heated to pre-reaction temperature of between 55° C. and 60° C. Next, 70.4 g of olefin was added quickly with the desired reaction temperature target being 77° C., measured using the temperature sensor located on the reaction chamber (similar location as temperature sensor 222a on reaction chamber 208). Next, the catalyst, paraffin, benzene and olefin were mechanically stirred for 40 minutes to complete the reaction. During the reaction, the temperature was maintained between 76° C. and 82° C. with target of 77° C. After completion of the reaction, the product was transferred to a separation vessel and the organic phase was separated. The organic phase was treated with 20 grams of CaO and mixed for an hour. The excess benzene was removed and the remaining product was then analyzed. The results of the analysis of the products are reflected in Table 3.

TABLE 3

| Example 3 | % 2-phenyl isomer |
|---|---|
| Run 11 | 14.6 |
| Run 12 | 14.6 |
| Run 13 | 15.2 |
| Run 14 | 14.7 |

The results of Table 3 show a low, controlled percentage of 2-phenyl isomer produced. The result in Run 13 may be due to the olefin feed plugged during its charge. However, in Run 11 the olefin feed also plugged during its charge.

What is claimed is:

1. An alkylation process comprising the steps of:
   providing a loop reactor comprising a reaction chamber and a heat exchanger, wherein the reaction chamber and the heat exchanger are in fluid communication with each other via at least one conduit such that a fluid in the reaction chamber can be circulated through the heat exchanger and returned to the reaction chamber;

introducing an alkylatable aromatic compound into the loop reactor;

introducing an olefin into the loop reactor;

introducing a catalyst into the loop reactor;

adjusting the alkylatable aromatic compound to a pre-reaction temperature that is below a desired reaction temperature prior to introducing the catalyst;

adjusting the olefin to a second pre-reaction temperature that is below the desired reaction temperature prior to introducing the catalyst;

optionally, adjusting the catalyst to a third pre-reaction temperature that is below the desired reaction temperature;

initially contacting the catalyst and olefin in the conduit circulating fluid from the reaction chamber to the heat exchanger;

circulating the alkylatable aromatic compound, the olefin and the catalyst in the loop reactor; and maintaining the alkylatable aromatic compound and olefin at the desired reaction temperature after contacting the catalyst and olefin, wherein adjusting the olefin to a second pre-reaction temperature that is below the desired reaction temperature occurs before the step of initially contacting the catalyst and olefin in the conduit circulating fluid from the reaction chamber to the heat exchanger, and wherein adjusting the alkylatable aromatic compound to a pre-reaction temperature that is below the desired reaction temperature comprises circulating the alkylatable aromatic compound through the heat exchanger.

2. The process of claim 1, further comprising mixing the alkylatable aromatic compound, the olefin and the catalyst in the loop reactor.

3. The process of claim 1, wherein the loop reactor further comprises a pump.

4. The process of claim 1, wherein adjusting the olefin to a second pre-reaction temperature that is below the desired reaction temperature comprises circulating the olefin through the heat exchanger prior to introducing the catalyst in the loop reactor.

5. The process of claim 1, wherein the pre-reaction temperature, second pre-reaction temperature and third pre-reaction temperature each comprise temperatures that are about 2 to about 60 degrees Celsius below the desired reaction temperature.

6. The process of claim 1, wherein introducing the catalyst into the loop reactor comprises adding the catalyst in the conduit circulating fluid from the reaction chamber to the heat exchanger.

7. The process of claim 1, wherein introducing the olefin into the loop reactor comprises adding the olefin in the conduit circulating fluid from the reaction chamber to the heat exchanger.

8. The process of claim 1, wherein the process further comprises the steps of:
introducing a diluent into the loop reactor; and
optionally, adjusting the diluent to a fourth pre-reaction temperature that is below a desired reaction temperature.

9. The process of claim 1, wherein the catalyst is an acid catalyst.

10. The process of claim 9, wherein the acid catalyst is selected from the group consisting of: hydrofluoric acid, triflic acid, aluminum chloride, boron trifluoride and combinations thereof.

11. The process of claim 1, wherein the alkylatable aromatic compound is selected from the group consisting of: benzene, xylene, toluene, cumene, ethylbenzene, butylbenzene, naphthalene and combinations thereof.

12. The process of claim 1, wherein the alkylatable aromatic compound comprises a substituted aromatic compound comprising the formula:

$$\text{R2} - \underset{}{\bigcirc} - \text{R3}$$
$$\text{R1}$$

wherein R1 is hydrogen or an alkyl group containing from about 1 to 4 carbon atoms; R2 is hydrogen or an alkyl group having from about 1 to 4 carbon atoms; and R3 is an alkyl group having from about 14 to about 60 carbon atoms.

13. The process of claim 1, wherein the olefin is at least one $C_8$ or higher olefin.

14. The process of claim 1, wherein the olefin is at least one $C_{14}$ to $C_{60}$ olefin.

15. The process of claim 1, wherein initially contacting the catalyst and olefin under conditions to control the temperature of the reaction of the catalyst and olefin comprises contacting the catalyst and olefin at a point before the catalyst and olefin pass through the heat exchanger.

16. The process of claim 1, wherein initially contacting the catalyst and olefin under conditions to control the temperature of the reaction of the catalyst and olefin comprises contacting the catalyst and olefin incrementally over a period of 1 minute to 120 minutes.

17. An alkylation process comprising the steps of:
providing a loop reactor comprising a reaction chamber and a heat exchanger, wherein the reaction chamber and the heat exchanger are in fluid communication with each other via at least one conduit such that a fluid in the reaction chamber can be circulated through the heat exchanger and returned to the reaction chamber;

introducing an alkylatable aromatic compound into the loop reactor;

introducing an olefin into the loop reactor;

introducing a catalyst into the loop reactor;

adjusting the alkylatable aromatic compound to a pre-reaction temperature that is below a desired reaction temperature prior to introducing the catalyst;

adjusting the olefin to a second pre-reaction temperature that is below the desired reaction temperature prior to introducing the catalyst;

optionally, adjusting the catalyst to a third pre-reaction temperature that is below the desired reaction temperature;

initially contacting the catalyst and olefin in the conduit circulating fluid from the reaction chamber to the heat exchanger;

circulating the alkylatable aromatic compound, the olefin and the catalyst in the loop reactor; and maintaining the alkylatable aromatic compound and olefin at the desired reaction temperature after contacting the catalyst and olefin, wherein adjusting the olefin to a second pre-reaction temperature that is below the desired reaction temperature comprises circulating the olefin through the heat exchanger prior to introducing the catalyst in the loop reactor and occurs before the step of initially contacting the catalyst and olefin in the conduit circulating fluid from the reaction chamber to the heat exchanger.

* * * * *